US012605056B2

(12) United States Patent
Spargo et al.

(10) Patent No.: US 12,605,056 B2
(45) Date of Patent: Apr. 21, 2026

(54) SUSPENSION CLEANING

(71) Applicant: Saban Ventures Pty Limited, Alexandria (AU)

(72) Inventors: Gavin Spargo, Lane Cove West (AU); Ingeborg Kristina Palmer, Lane Cove West (AU)

(73) Assignee: Saban Ventures Pty Limited, Macquarie Park (AU)

( * ) Notice: Subject to any disclaimer, the term of this patent is extended or adjusted under 35 U.S.C. 154(b) by 678 days.

(21) Appl. No.: 16/771,914

(22) PCT Filed: Dec. 6, 2018

(86) PCT No.: PCT/AU2018/051309
§ 371 (c)(1),
(2) Date: Jun. 11, 2020

(87) PCT Pub. No.: WO2019/113635
PCT Pub. Date: Jun. 20, 2019

(65) Prior Publication Data
US 2021/0068643 A1 Mar. 11, 2021

(30) Foreign Application Priority Data
Dec. 11, 2017 (AU) ................................. 2017904966

(51) Int. Cl.
*A61B 1/12* (2006.01)
*A61L 2/18* (2006.01)

(52) U.S. Cl.
CPC ................ *A61B 1/121* (2013.01); *A61L 2/18* (2013.01); *A61L 2202/17* (2013.01); *A61L 2202/24* (2013.01)

(58) Field of Classification Search
CPC .... A61L 2/18; A61L 2202/17; A61L 2202/24; A61B 1/121; A61B 2090/701;
(Continued)

(56) References Cited

U.S. PATENT DOCUMENTS 5,985,038 A * 11/1999 Dawson ................. A61B 1/123
134/1
6,326,340 B1 * 12/2001 Labib ....................... C11D 3/48
510/370
(Continued)

FOREIGN PATENT DOCUMENTS

EP 2147656 A1 1/2010
WO WO-2004000475 A1 * 12/2003 ........... B08B 9/0556
(Continued)

OTHER PUBLICATIONS

"Energy Conservation in Ice Slurry Application," Leiper et al., 2013, Applied Thermal Engineering, 51:1255-1262 (Year: 2013).*
(Continued)

*Primary Examiner* — Douglas Lee
(74) *Attorney, Agent, or Firm* — Edell, Shapiro & Finnan, LLC

(57) ABSTRACT

A method of cleaning a contaminated surface, such as cleaning the elongate interior lumen of an endoscope contaminated with flesh, bone, blood, mucous, faeces or biofilm, said method comprising the steps of: providing a suspension of solid particles in a liquid to said contaminated surface, and flowing said suspension along said surface thereby to remove contaminant from the surface. The suspension is preferably an ice slurry, where the solid material
(Continued)

is ice crystals. The slurry preferably has a solid fraction between 50-85% by volume. A freezing point depressant may be present.

16 Claims, 4 Drawing Sheets

(58) Field of Classification Search
CPC ......... A61B 90/70; B08B 9/057; B24C 1/003; B24C 3/327
See application file for complete search history.

(56) References Cited

U.S. PATENT DOCUMENTS

| | | | |
|---|---|---|---|
| 6,916,383 B2 | 7/2005 | Quarini | |
| 7,435,426 B2 | 10/2008 | Einziger et al. | |
| 2003/0121532 A1 | 7/2003 | Coughlin et al. | |
| 2003/0140944 A1* | 7/2003 | Quarini | B08B 9/0556 |
| | | | 134/22.12 |
| 2010/0212336 A1* | 8/2010 | Chapman | F25C 5/20 |
| | | | 62/99 |
| 2016/0081756 A1 | 3/2016 | Sommacal | |
| 2017/0274011 A1* | 9/2017 | Garibyan | A61K 31/045 |

FOREIGN PATENT DOCUMENTS

| | | |
|---|---|---|
| WO | WO-2017198684 A1 * | 11/2017 |
| WO | 2018064284 A1 | 4/2018 |

OTHER PUBLICATIONS

Ainslie et al., "Heat Exchanger Cleaning Using Ice Pigging," Jun. 14-19, 2009, Proceedings of Int'l. Conference on Heat Exchanger Fouling and Cleaning VIII-2009, Schladming, Australia, pp. 433-438.

Leiper et al., Energy Conservation in Ice Slurry Application, 2013, Applied Thermal Engineering, 51:1255-1262, Abstract ony.

Shire et al., "Pressure Drop of Flowing Ice Slurries in Industrial Heat Exchangers," 2009, Applied Thermal Engineering, 29:1500-1506, Abstract ony.

International Search Report and Written Opinion Issued Feb. 13, 2019 in PCT/AU2018/051309, 13 pages.

European Search Report, Application No. 18889858.9, dated Aug. 5, 2021, 6 pages.

Communication under Rule 71(3) EPC in counterpart European Application No. 18889858.9-1113, mailed Mar. 3, 2025, 5 pages.

* cited by examiner

SUSPENSION CLEANING

REFERENCE TO RELATED APPLICATIONS

This application is the 371 National Stage Application of International Application No. PCT/AU2018/051309, filed Dec. 6, 2018, which claims priority to Australia Patent Application No. 2017904966, filed Dec. 11, 2017, the entire contents of which are incorporated herein by reference.

TECHNICAL FIELD

This invention relates to methods for cleaning the interior cavities and lumens of devices, and in particular for cleaning the lumens of contaminated medical instruments.

The invention has been developed primarily for use in the cleaning the interior lumens of endoscopes and will be described hereinafter to reference to this application. However, it will be appreciated that the invention is not limited to this particular field of use.

BACKGROUND ART

An endoscope is an elongate tubular instrument that may be rigid or flexible and which incorporates an optical or video system and light source. Typically, an endoscope is configured so that one end can be inserted into the body of a patient via a surgical incision or via one of the natural openings of the body. Internal structures near the inserted end of the endoscope can be thus be viewed by an external observer.

As well as being used for investigation, endoscopes are also used to carry out diagnostic and surgical procedures. Endoscopic procedures are increasingly popular as their minimally invasive nature provides a better patient outcome (through reduced healing time and exposure to infection) and also enables hospitals and clinics to achieve higher patient turnover.

Endoscopes typically take the form of a long tube-like structure with a 'distal tip' at one end for insertion into a patient and a 'connector end' at the other with a control handle at the centre of the length. Typically, the connector end is hooked up to a supply of light, water, suction and pressurised air. The control handle is held by the operator during the procedure to control the endoscope via valves and control wheels. The distal tip contains the camera lens, lighting, nozzle exits for air and water, exit point for suction and forceps.

All endoscopes have internal channels used either for delivering air and/or water, providing suction or allowing access for forceps and other medical equipment required during the procedure. Some of these channels run from one end of the endoscope to the other while others run via valve sockets at the control handle. Some channels bifurcate while and others join from two into one.

Endoscopes used for diagnostic or surgical purposes contain a long, narrow lumen (sometimes referred to as a forceps channel) through which surgical apparatus can pass. The apparatus can be used to remove diseased tissue or collect tissue samples for diagnosis. The collected tissue is then removed from the endoscope by drawing it outwards through the lumen. As a consequence, the lumen can become contaminated with traces of tissue from the patient. Blood, mucus and faecal matter can also readily find their way into the lumen.

The high cost of endoscopes means they must be re-used. Because of the need to avoid cross infection from one patient to the next, each endoscope must be thoroughly cleaned and disinfected or sterilised after each use. This involves the cleaning of not only the outer skin of the endoscope, but also cleaning and disinfecting the lumen. Endoscopes used for colonoscopic procedures are approximately two meters long and have one or more lumen channels of diameter no more than a few (2-4) millimetres. Ensuring that such long narrow channels are properly cleaned and disinfected between patients presents a considerable challenge.

The challenge of cleaning is also made more difficult by the fact that there is not just one configuration for endoscopes. There are a variety of endoscopic devices suited to the particular cavity to be investigated i.e. colonoscopes inserted into the colon, bronchoscopes inserted into the airways, gastroscopes for investigation of the stomach. Gastroscopes, for instance, are smaller in diameter than colonoscopes, bronchoscopes are smaller again and shorter in length, while duodenoscopes have a different tip design to access the bile duct, and so on.

Some endoscopes, such as duodenoscopes, also possess a "blind lumen", closed at one end which can be even more difficult to clean.

A variety of options are available to mechanically remove biological residues from the lumen, which is the first stage in the cleaning and disinfection process. By far the most common procedure for cleaning the lumens using small brushes mounted on long, thin, flexible lines. Brushing is the mandated means of cleaning the lumen in some countries.

These brushes are fed into the lumens while the endoscope is submerged in warm water and a cleaning solution. The brushes are then pushed/pulled through the length of the lumens in an effort to scrub off the soil/bio burden. Manual back and forth scrubbing is required. Water and cleaning solution is then flushed down the lumens. These flush-brush processes are repeated three times or until the endoscope reprocessing technician is satisfied that the lumen is clean. At the end of this cleaning process air is pumped down the lumens to dry them.

A flexible pull-through having wiping blades may also be used to physically remove material. A liquid flow through the lumen at limited pressure can also be used.

In general, only the larger suction/biopsy lumens can be cleaned by brushing or pull throughs. Air/water channels are too small for brushes so these lumens are usually only flushed with water and cleaning solution.

After mechanical cleaning, a chemical clean is carried out to remove the remaining biological contaminants. Because endoscopes are sensitive and expensive apparatus, the biological residues cannot be treated at high temperatures or with strong chemicals. For this reason, the mechanical cleaning needs to be as thorough as possible.

In many cases, the current mechanical cleaning methodologies fail to fully remove biofilm from lumens, particularly where cleaning relies on liquid flow alone.

Regardless of how good the conventional cleaning processes are, it is almost inevitable that a small microbial load will remain in the channel of the lumen. There has been significant research to show that the method of cleaning with brushes, even when performed as prescribed, does not completely remove biofilm in endoscope lumens.

As well as lacking in efficacy, the current manual brushing procedures suffer from other drawbacks.

The large number of different endoscope manufacturers and models results in many minor variations of the manual cleaning procedure. This has led to confusion and ultimately poor compliance in cleaning processes.

The current system of brushing is also hazardous to the endoscope reprocessing staff who clean them. Brushing can disperse small particles or aerosols of bioburden into the air which can be accidentally ingested or inhaled. The chemicals that are currently used to clean endoscopes can adversely affect the reprocessing staff.

The current system of manual brushing is also labour intensive, leading to increased cost.

Thus, the current approaches to cleaning and disinfecting the lumens in medical apparatus are still inadequate and residual microorganisms are now recognised as a significant threat to patients and staff exposed to these devices. There is evidence of bacterial transmission between patients from inadequate cleaning and disinfection of internal structures of endoscopes which in turn has led to patients acquiring mortal infections. Between 2010 and 2015 more than 41 hospitals worldwide, most in the U.S., reported bacterial infections linked to the scopes, affecting 300 to 350 patients (http://www.modernhealthcare.com/article/20160415/NEWS/160419937)

It would be expected that a reduction in the bioburden in various medical devices would produce a concomitant overall reduction in infection rates and mortality.

In addition, if endoscopes are not properly cleaned and dried, biofilm can build up on the lumen wall.

If an endoscope is not properly cleaned and dried, biofilm can form on the interior surfaces of the device. Biofilms start to form when a free floating microorganism attaches itself to a surface and surrounds itself with a protective polysaccharide layer. The microorganism then multiplies, or begins to form aggregates with other microorganisms, increasing the extent of the polysaccharide layer. Multiple sites of attachment can in time join up, forming significant deposits of biofilm.

Once bacteria or other microorganisms are incorporated in a biofilm, they become significantly more resistant to chemical and mechanical cleaning than they would be in their free floating state. The organisms themselves are not inherently more resistant, rather, resistance is conferred by the polysaccharide film and the fact that microorganisms can be deeply embedded in the film and isolated from any chemical interaction. Any residual biofilm remaining after an attempt at cleaning quickly returns to an equilibrium state and further growth of microorganisms within the film continues.

Endoscopes lumens are particularly prone to biofilm formation. They are exposed to significant amounts of bioburden, and subsequent cleaning of the long narrow lumens is quite difficult due to inaccessibility and the inability to monitor the cleaning process. There is considerable pressure in medical facilities to reprocess endoscopes as quickly as possible. Because endoscopes are cleaned by hand, the training and attitude of the technician are important in determining the cleanliness of the device.

Residual biofilm on instruments can result in a patient acquiring an endoscope acquired infection. Typically, these infections occur as outbreaks and can have fatal consequences for patients.

It is an object of the present invention to overcome or ameliorate at least one of the disadvantages of the prior art, or to provide a useful alternative.

Any discussion of the prior art throughout the specification should in no way be considered as an admission that such prior art is widely known or forms part of common general knowledge in the field.

SUMMARY OF THE INVENTION

According to a first aspect the invention provides a method of cleaning a contaminated surface of a medical instrument, said method comprising the steps of: providing a suspension of solid particles in a liquid to said contaminated surface, and flowing said suspension along said surface thereby to remove contaminant from the surface.

The surface of a medical instrument may be the interior surface of a medical instrument, such as endoscope. More particularly, the interior surface is an elongate lumen.

The contaminant may, for example, be flesh, bone, blood, mucous, faeces or biofilm.

The suspension may be flowed continuously in a single direction, or pulsed or the suspension may be flowed alternately in different directions.

The flow rate used is normally the maximum allowable as determined by the pressure rating of the instrument.

The method may also further include a rinsing step.

In one embodiment, the solid particles are ice particles. Preferably, the solid particles are ice particles and the liquid is water. Preferably, the suspension of solid particles is a slurry of ice particles in water.

The slurry may also comprise ice particles, water and a freezing point depressant, such as for example, ethanol, ethylene glycol, propylene glycol or salt brine.

Preferably, the slurry comprises an ice fraction of 50-85% by weight, more preferably, 80-85% by weight.

The flow rate used is normally the maximum allowable as determined by the pressure rating of the instrument, which translates to a flow rate of less than 10 cm/s.

The ice particles may be made by partial freezing of the water, or by combining comminuted ice with water.

The ice particles may for preference have a particle size of 1 to 250 microns, or more preferably 10 to 50 microns.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "cleaning" as used herein is intended to refer to the removal of inorganic and organic matter, including but not limited to bio burden, microorganisms, biofilm and other foreign objects such as surgical clips.

DESCRIPTION OF THE INVENTION

Figure 1:
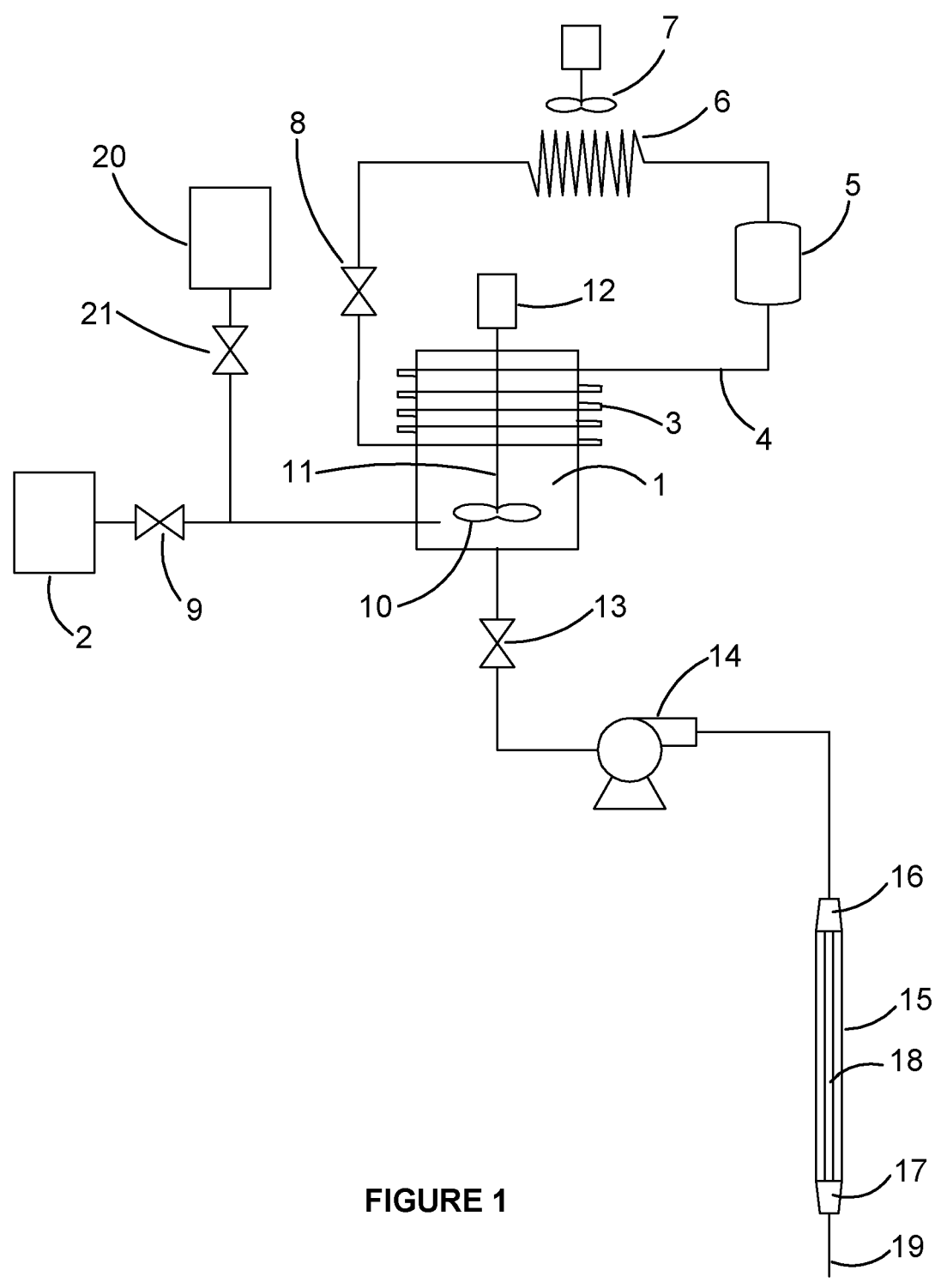
FIG. 1 shows an ice slurry cleaning prototype.

The present invention in it broadest form relates to passing a suspension of solid particles in a liquid through the lumen of an endoscope for the purposes of mechanically cleaning the endoscope channel of bioburden, which includes residual tissue such as flesh, bone, blood, mucous and faeces remaining after diagnostic or surgical procedures. The present invention also relates to the use of suspensions to remove biofilm.

The invention will be described with reference to the use of an ice/water slurry for lumen cleaning. Based on the teaching of the present invention it will be understood by those skilled in the art of that the invention may be embodied in other forms and may utilise other liquids and other particles in the cleaning of endoscope lumens, and other instruments and surfaces without departing from the concepts herein described.

For instance, the methods of the present invention are useful in cleaning other lines susceptible to contamination. Particularly, the methods of the present invention are useful in cleaning water lines, such as those used in the food, beverage, manufacturing or airconditioning industries. Such lines are very susceptible to biofilm contamination.

Ice Slurry Cleaning

The invention will now be first described with reference to the cleaning of the lumen of an endoscope by a slurry of ice in water.

To the best of the Applicant's knowledge, slurries have not previously been used to clean medical equipment such as endoscopes. Quirini (U.S. Pat. No. 6,916,383) used discrete agglomerates of ice (usually not more than 20 times longer than their width) to form ice "pigs", which act as semi solid boluses to clean or block pipes. Because the ice pigs, unlike conventional cleaning pigs, are meltable the problems of blockage and recovery from pipes could be avoided.

In a first particularly preferred embodiment of the present invention, the suspension is in the form of a slurry which comprises water-ice crystals in a fluid. The slurry is pumped through the endoscope to provide a physical clean of the endoscope lumen.

In some cases, the fluid is water and the slurry is an ice/water slurry. However, in other cases, it is desirable to add a freezing point depressant to ensure that the ice does not melt prior to completing the necessary cleaning function. Suitable freezing point depressants include glycols, such as ethylene glycol or propylene glycol, alcohols such as methanol, ethanol or salts such as sodium chloride, calcium chloride, or the sodium or potassium salts of acetate or formate. Any suitable freezing point depressant that does not damage lumen walls can be used.

The ice fraction is desirably around 50-85% of the slurry by volume, and more advantageously around 80-85%. The slurry is difficult to handle and pump at solids volumes above 85%. Using quantities of ice below 50% does not provide sufficient cleaning, since the solid volume at that low level is not sufficient to result in forceful mechanical contact between the solids and the contaminants on the lumen wall. With high liquids content, the solid particles are free to simply slide or float past the contaminant. When the solid fraction is increased, particularly in a confined lumen, the solid particles interact in such a way that those particles at the surface are not free to slide or float past the contaminant, but are in fact forced into it in such a manner that the ice crystals abrade the bioburden or biofilm.

Ideally, it is beneficial to allow the slurry to move through the endoscope lumen as fast as possible. The maximum speed of the slurry is dictated by the need to ensure that the pressure at which the slurry is fed into the endoscope does not exceed the operational pressure of the endoscope. Thus, the slurry is fed at or near the maximum working pressure of the endoscope. In practice, this means that the flow rate of the ice slurry is typically below 10 cm/s.

Ice morphology is believed to have an effect upon cleaning efficacy. Preliminary investigations indicate that rounded particles are more effective than angular particles as the angular particles do not flow as well for the same particle size. Similarly, particles that are too large are difficult to pump and do not provide sufficient granularity to evenly scour the entire endoscope wall, whereas particles that are too small tend to exhibit more fluid like properties, rather than the necessary solid abrasion required. Particles will ideally be within the range of 1 to 250 microns, and more particularly, 10 to 50 microns.

The ice crystals can be made by the partial freezing of the carrier fluid, or by comminuting ice with water, or a combination thereof. Ice slurries can be conveniently and consistently generated by commercial "slushie" machines which are used to make commercial refreshments. These typically use a freezing vat the contain and freeze the water, however, the sides of the vat are continually scraped and stirred by an auger, allowing the formation of new, small ice crystals on the wall of the vat that are dislodged and return to the liquid. This is repeated until the material in the freezing vat has the desired ice water ratio. These machines allow a degree of control over the size of the crystals, which can be controlled by the cooling rate and the auger speed. Larger crystals can be made by slowing the auger or increasing the cooling rate or both.

Once the ice/water slurry has been generated, it is then passed into the endoscope for cleaning. The general process is illustrated with respect to FIG. 1. In FIG. 1, slurry tank 1 is supplied by water supply 2. Slurry tank 1 is also equipped with a cooling coil 3. Cooling coil 3 may run around the outside of the tank, or be disposed within the walls, or be wholly or partially within the tank. Cooling coil 3 can be reduced in temperature by means of a conventional refrigeration circuit 4 powered by a compressor 5, a heat sink 6 and heat dispersion fan 7, and an expansion valve 8.

Inlet valve 9 is opened leading to water to flow from water supply 2 to slurry tank 1. The tank contains a mixing auger 10, attached by shaft 11 to a mixing motor 12. Water enters the slurry tank 1 and is cooled by the activation of the cooling coil 3. When the water reaches a suitable temperature, motor 12 is activated and the blade 10 begins to rotate. As the water reaches 0° C., it begins to freeze. The auger 10 acts upon the ice crystals formed on the side of the tank to scrape them from the wall and to prevent the formation of large aggregates of ice.

The rate of cooling, and the configuration of the cooling tank, the maturation of the mixture and the speed and design of the slurry apparatus all influence the crystal morphology. However, good results could be obtained for a variety of crystal morphologies, with crystals having a sharp or irregular microstructure being preferred over rounded crystals.

Once a slurry has been formed that contains suitable crystals and has an ice fraction of 50-85%, ideally 80-85%, it is ready for use. Slurry outlet valve 13 is opened and the slurry exits the slurry tank 1. The slurry is further pumped by slurry pump 14. The slurry is pumped into endoscope 15 which is held in place by connectors 16 and 17. The slurry flows down the lumen of endoscope 18 and is discharged via exit line 19 into a drain.

The slurry is pumped down the lumens at the maximum pressure permissible by the endoscope manufacturer. A typical maximum allowable air or water pressure for aerating or irrigating endoscope channels is around 0.5 MPa (5 kgf/cm$^2$, 71 psig). At this pressure, the flow rate for a slurry is less than 10 cm/s, which is considerably less than the flow rate of water used to flush the channel.

After passing through the lumen, the slurry is discharged into a drain along with the dislodged contaminants. The slurry can be allowed to melt and the water then filtered or centrifuged to remove the residual material dislodged from the lumen. The residual material can be removed and treated as biological waste. The water can be further sterilised if desired and discharged as necessary.

The water may also contain chemicals to alter the characteristics of the slurry. For example, freezing point depressants, such as e.g. ethanol, propylene glycol, salt brine, may be used. Other agents, such as surfactants, disinfectants, residual treatments etc may also be added to the slurry for beneficial effect. If used, the freezing point depressants or other chemicals may be stored in a chemical tank 20 and can be introduced into the slurry tank as desired by opening valve 20.

In one embodiment, the flow of the slurry may be in a single direction at a constant rate. Alternatively, the flow may be pulsed, in that it moves, rests for a period and then continues to move in the same direction, with that being repeated. Alternatively, in another embodiment, the flow of the slurry at times is intermittently reversed, creating a back and forth scrubbing motion of the solid particles which aids in removing residual bioburden or biofilm that may have been flattened in a particular direction by the flow of the slurry in the primary direction (from the reservoir towards the discharge point of the endoscope. In yet a further embodiment, the flow may be fed through the endoscope in an alternating manner with one or more other liquid, gas or slurry flows. For instance, a chemical clean may be included between slurry flow phases to assist in the removal of residues.

The slurry is passed through the endoscope for a suitable time to remove the biological material, depending upon the initial level of contamination and the construction of the endoscope. Once the slurry cleaning has finished, the lumen of the endoscope can be flushed with water and air dried, or dried in any other suitable manner.

Experimental

1. Test Soils and Contaminants

The removal of bioburden from endoscope lumens was modelled using a variety of standard and customised test soils applied to the inner surfaces of teflon or other suitable tubing in order to mimic the inner lumens of endoscopes. The soils were pumped into the tube or manually applied to the inner surfaces of the tubes and allowed to dry or bake onto the surface as required. In addition to modelling soils, the present inventors also employed standardised protocols for biofilm for testing and residual protein.

The procedures for soil preparation, as well as the fixed protein and biofilm contaminations are as follows:

A. Soil 5B (Pumped Soil)

Soil 5B is a standardised pumped test soil for use in experiments in the cleaning of medical devices.

Ingredients:

3 g hog mucin 5 ml horse blood 1.5 ml deionised water 50 ml egg yolk 3.0 g of mucin was mixed with 5 mL of horse blood and stirred until smooth, 1.5 mL of deionised water was added and the mixture again fully stirred. 5×10 mL batches of egg yolk were added to the mixture while stirring. The mixture was stored in a cool dry environment in a closed container.

Teflon tubes (ID 4.25 mm, OD 5.1 mm, 10 cm long) were inoculated by pumping the soil into the tube with a syringe, holding the soil in position for 5 seconds and then pumping the soil back into the syringe.

The inoculated tubes were fixed in place inside a small container. The container was then placed on top of a rotational mixing apparatus situated inside an incubator. The tubes were rotated at medium speed in the incubator for 30 minutes at 40° C. The tubes were then connected to a 4 port air pump machine (eight tubes at a time via four T-Pieces) within the 40° C. incubator. The tubes were held in the incubator for a further 15 minutes at low airflow. Any tubes that leaked during the airflow stage were discarded. The tubes were stored in a cool dry environment.

B. Soil 5D (Brushed Soil)

Soil 5D is a standardised brushed test soil for use in experiments in the cleaning of medical devices.

Ingredients:

3 g hog mucin 5 ml horse blood 1.5 ml deionised water 50 ml egg yolk 3.0 g of mucin was mixed with 5 mL of horse blood and stirred until smooth, 1.5 mL of deionised water was added and the mixture again fully stirred. 5×10 mL batches of egg yolk were added to the mixture while stirring. The mixture was stored in a cool dry environment in a closed container.

Teflon tubes (ID 4.25 mm, OD 5.1 mm, 10 cm long) were inoculated one at a time. A small brush was dipped into the soil and then passed through the inside of the tube several times from each direction until an even coating is achieved. The brush was removed along with any soil that builds up around the ends of the tube and any that is on the exterior of the tube.

For the purposes of the present invention, soil was applied to attain a target weight of between 0.0685 g and 0.0925 g.

The inoculated tubes were placed in an incubating oven for 5 minutes at 40° C. Advantageously, the tubes were used immediately. If necessary, the tubes could be stored during down time in testing in a zip-lock bag with as much air removed as possible.

C. ATS2015

ATS2015 is a commercially available artificial test soil used as to model, available from Healthmark Industries Co. It contains haemoglobin, protein, carbohydrate lipids and insoluble fibres and is used as a standardized test soil in proportion found on clinically used medical devices, including specifically flexible endoscopes.

Ingredients:

ATS2015 dry powder—0.0905 g per mL final volume

Defibrinated blood (sheep)—0.2 mL per mL final volume

Sterile water—1 mL per mL final volume

Water was added to the ATS 2015 dry powder and vortexed/shaken for 10 minutes or until completely mixed. The foam was allowed to settle for 20 minutes. The blood was added and mixed gently.

When preparing ATS2015 soil for biological testing, a microbe containing suspension was added after the dry powder had been dissolved. The amount of water used to introduce the microbe suspension was noted in advance, so the final volume of sterile water was still only 1 mL The reconstituted mixture could be satisfactorily stored in an air-tight container at 2-5° C., away from light and heat for up to two weeks.

Soil was pumped into Teflon tubes (ID 4.25 mm, OD 5.1 mm, 10 cm long) using a syringe. The tube was completely filled soil. The tubes were held vertically to allow draining, with a small volume of air applied to the top of the syringe at the completion of the draining process. The inoculated tubes were allowed to dry on a bench at room temperature (15-25° C.) for 1 hour. Cleaning tests were conducted within 1 hour of preparation.

D. Black Soil

Black soil is a standard test soil described in ISO/TS 15883-5:2005(E) useful in experiments relating to the cleaning of medical devices.

Ingredients:

30 g unbleached plain wheat flour 15 g water soluble wallpaper adhesive powder 1 hens egg (60-65 g)

10 ml black ink (water tolerant/permanent, Indian ink)

240 ml water

The ingredients above were mixed together to form a uniform thick paste. The paste could be used immediately or stored in an air-tight container at 2-5° C. for up to one month.

Black soil at room temperature was pumped into Teflon tubes (ID 4.25 mm, OD 5.1 mm, 10 cm long) via a syringe. The syringe plunger was rapidly withdrawn to extract excess soil such that there was a thick, uniform coating of soil on the inside of the lumen with an unbroken air-path from one end of the tube to the other. Unsuitable tubes were refilled or discarded. The inoculated tubes were allowed to dry on a bench at room temperature (15-25° C.) for 30-35 minutes and used within a subsequent 30 minute period.

E. Edinburgh Soil

Edinburgh soil is a standard test soil described in ISO/TS 15883-5:2005(E) for use in experiments in the cleaning of medical devices.

Ingredients:

100 ml fresh egg yolk 10 ml defibrinated blood (horse or sheep)

2 g dehydrated hog mucin

The above ingredients were mixed together to give a liquid of uniform consistency. The liquid was used immediately or stored in an air-tight container at 2-5° C. for up to a week.

Soil at room temperature was pumped into Teflon tubes (ID 4.25 mm, OD 5.1 mm, 10 cm long) via a syringe. The tubes were held vertically to allow excess soil to drain. The last traces of bulk soil were removed using a syringe to push a small amount of air through the tube. The inoculated tubes were allowed to dry on a bench at room temperature (15-25° C.) for between 30 and 120 minutes.

F. Fixed Protein

Ingredients:

1% glutaraldehyde

1% horse serum

Equipment:

1% horse serum was pumped through a Teflon tubes (ID 4.25 mm, OD 5.1 mm). The volume used was 2×tube volumes. After 20 minutes, 2×tube volumes of 1% glutaraldehyde was pumped through the tube. After 10 minutes, the process was repeated. Altogether, there were five cycles of horse serum followed by five cycles of glutaraldehyde. The tube was then washed with 10 tube volumes.

The tube was stained for protein as disclosed below, and could be cut into 10 cm lengths.

G. Biofilm

This procedure outlines the preparation and growth of biofilm of *Pseudomonas aeruginosa* ATCC15442 in tubes for use in experiments in the cleaning of medical devices.

*Pseudomonas aeruginosa* ATCC15442 culture was grown overnight in Synthetic Broth+Glucose (5 mL) at 37° C. The microbial inoculant concentration was determined by % transmission by spectrophotometry at 580 nm wavelength. The level of inoculum was also determined by historical data.

All apparatus were sterilised before use and the conditions used were aseptic. Teflon tubes (ID 4.25 mm, OD 5.1 mm, up to 5 metres long) used for inoculation were sterilized in an autoclave.

5% TSB (tryptic soy broth, equates to 50 mL/L) in 1 L of sterile distilled water was inoculated with ~0.2% of *P. aeruginosa* isolated culture. The exact volume of microorganism added was dependent on the % Transmission). The inoculated growth medium was placed into a 1 L Schott bottle, which was stirred.

The inoculated media 200 was then pumped via pump 201 at the lowest available flow setting (~5 L/min) such that the growth media was transferred from the Schott flask 202, through teflon tube 203 to be inoculated and then back into the Schott flask. The Schott flask 202 and teflon tube 203 were immersed in a water bath 204 at 30° C., such that the inoculated grown medium was contained below the level of the water bath and always maintained at 30° C. by heater 205. The apparatus was checked to ensure that there were no bubbles in the teflon tubing and that the inoculated grown medium was in contact with every part of the internal of the tube as it flowed through.

Figure 3:
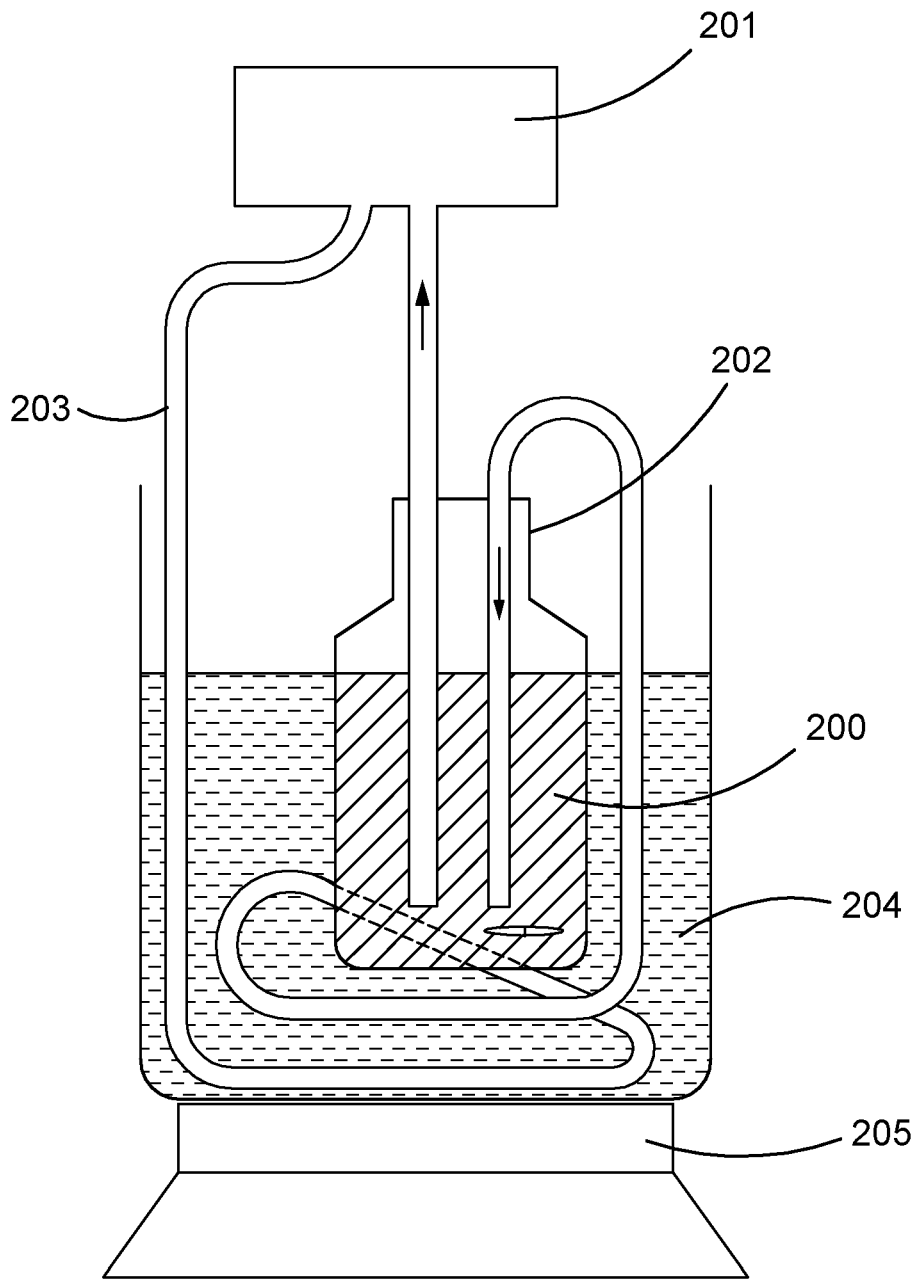
FIG. 3 is shows an arrangement used to produce standardised biofilm deposits in a lumen.

The setup, which shows the water cycling in the closed system immersed in the waterbath, is shown in FIG. 3

Growth Cycle:

After 48 hours, the pump was stopped and the growth medium was allowed to empty from the tube at a slow rate. The growth medium was replaced, the tube refilled and the pump restarted After a further 72 hours, the tube was again drained and the growth medium replaced. The pump was restarted and allowed to run for a further 48 hours, after which the tubing was removed and drained and was ready for testing. The inoculated tubing could be stored overnight at −4° C. The tubing could be cut to desired lengths and tested.

2. BioBurden Test Protocols

Testing for the presence of residual bioburden in the enclosed parts of medical instruments is challenging. In consequence, there is little available in the way of established protocols for assessing either the quantity or the activity of biological residue. The Applicant has developed the following tests which enable rapid and reproducible quantification of biological residues.

2.1. Procedure for Determination of Cleaning Efficacy by Weight.

The following procedure is used on each sample, with at least 2 replicates:

Step 1. The unsoiled item is weighed.

Step 2. Test soil is applied to the item.

Step 3. The soiled item is weighed. Items with more than ±10% deviation from mean mass were not used for testing but retained for % dried calculation. At least one soiled item was retained as a standard for % dried calculation.

Step 4. The cleaning experiment on the item was conducted. After cleaning, the item was allowed item to drain Step 5. Cleaned tubes and soiled standards were placed in a container containing dry silica in an oven at 56° C.

Step 6. The dried item was weighed after 1 day.

Step 7. The dried item was weighed after 3-5 days. Weighing was repeated until dried items attained a constant weight. (Drying time depends on the amount and distribution of soil in the item, the extent of moisture present and the air accessibility of the soil).

Step 8. The mass of soil removed by cleaning was obtained by the following formulae:

The mass removed by drying, per unit-mass of initial soil, from the drying control tubes was calculated by the following equation and their average determined:

$$\text{DryCal} = M_{init\ soil} / (M_{tube\ dry} - M_{tube\ unsoiled})$$

$$\text{Where:} M_{init\ soil} = (M_{tube\ soiled} - M_{tube\ unsoiled})$$

The percentage of soil removed is then calculated by the following equation:

$$M_{soil\ removed}=(M_{init\ soil}-((M_{tube\ dry}-M_{tube\ unsoiled})\\ *DryCal_{ave}))/M_{init\ soil}$$

2.2 Procedure for Protein Staining of Lumens

The following procedure was used to stain protein residues for visual inspection:

Ingredients:

50% Methanol or EtOH

10% Glacial acetic acid 0.5% Coomassie G-250 (dehydrated)

40% H20

The above ingredients were combined and mixed well.

The stain was drawn into a syringe and filled into the tubes to be tested for residual protein. The tubes were then flushed with water until the solution colour exiting the tube was clear. Residual protein could be detected in the locations where the tube remained blue.

Uncontaminated tubing was subjected to the staining process and used as a control.

3. Cleaning by Ice Slurry

Initial experiments with ice clearing slurries demonstrated that the solid fraction, that is the ratio of ice or other solids to the liquid phase, had a significant impact on the cleaning ability of the slurry. The present applicants conducted a number of experiments to quantify the relationship between solid fraction and cleaning ability. The cleaning efficacy of an ice slurry pumped through a lumen with respect to the solid fraction was measured.

3.1 Determination of Ice Solid Fraction

In the particular embodiment tested, the ice solution used comprised ethylene glycol as freezing point depressant and tap water. Ethylene glycol was added to water to produce an aqueous mixture with a refractometer reading of 15 brix and the mixture introduced into the slurry machine. Further water was added to reduce the refractometer reading to 5 brix and the ice slurry machine was allowed to reach a constant state.

A plunger filter moveable inside a cylindrical barrel was used. Ice from a commercial ice slurry machine (around 300-400 ml) is placed into the cylindrical vessel and the mass of the slurry ($M_{slurry}$) recorded. The plunger was the used to compress the ice slurry and the liquid was then decanted from the solid ice phase. The liquid was then discarded and the solid fraction weight ($M_{ice}$) was then determined. The base solid fraction, i.e. the maximum solid fraction producible by the ice machine, can thus be calculated from the following equation:

Base Solid Fraction mass=$(M_{ice})/M_{slurry}$.

Figure 2:
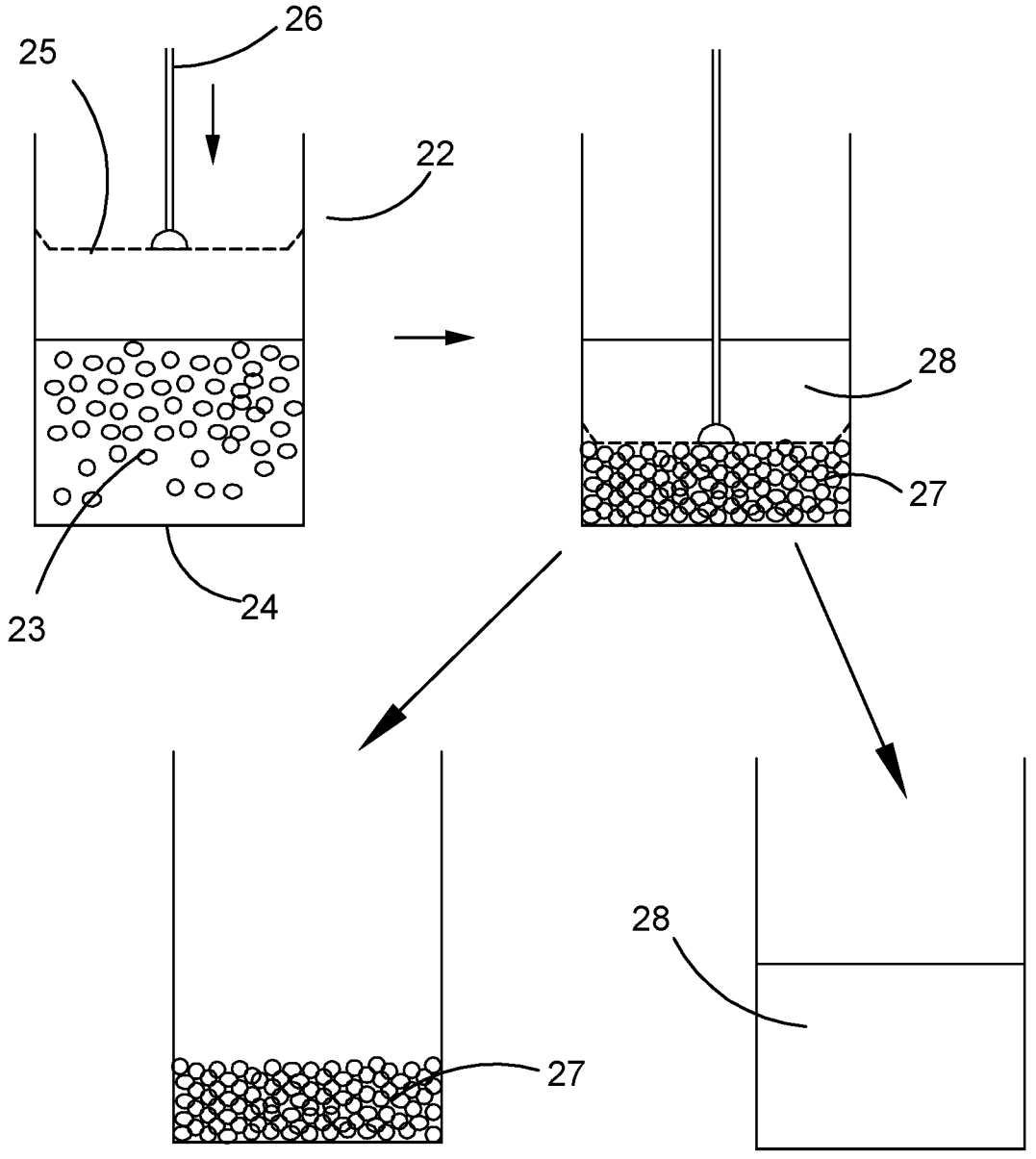
FIG. 2 shows an arrangement used to determine ice solid fraction in a water/ice slurry.

FIG. 2 shows apparatus 22 used to separate ice crystals from water in a consistent manner to determine the solid fraction of a slurry. Ice slurry 23 is placed into cylinder 24. A screen 25 with cross section matched to cylinder 25 is placed in the cylinder and depressed downwardly by plunger 26. As the plunger moves downwardly, the solid fraction of the ice 27 is compressed and the liquid fraction 28 remains above the screen 25. The liquid fraction 28 can then be decanted and the solid faction 27 retained. The liquid and solid fractions can thus be weighed separately.

An ice slurry of a predetermined Target Solid Fraction was then prepared by partial compression of the ice slurry and the removal of a specific volume of liquid according to the solid fraction being targeted according to the following equation:

$M_{liquid\ remove}$=Target Solid Fraction mass($M_{slurry}$)− Base Solid Fraction mass($M_{slurry}$).

Repeated procedures showed the above processes to produce very consistent and reproducible results.

3.2 Ice Slurry Cleaning Process

In order to determine the cleaning efficacy of ice slurry cleaning, a water bath was set to 36° C. and a small jar filled with de-ionised water was placed in the water bath. This water was then continuously pumped via a peristaltic pump at 132 ml/min through the blank, unsoiled tube (10 cm teflon tube, ID 4.25 mm, OD 5.1 mm and back into the small jar to maintain the temperature of the pump and plumbing close to the water bath temperature.

10 cm lengths of teflon tube, ID 4.25 mm, OD 5.1 mm, were soiled with Soil 5B as outlined in the procedure described elsewhere in this document. A minimum of 3 soiled lumens were put aside as drying controls.

Each soiled tube was then used to replace the blank tube in the peristaltic pump. The soiled tube was allowed to soak for 4 minutes.

A slurry with the required Target Solid Fraction was then transferred as quickly as possible to a 60 cc syringe with modified tip to allow direct attachment to a lumen test piece. The outlet of the syringe is connected to the test lumen and the barrel of the syringe is propelled in an automated manner (by a modified electric caulking gun at maximum power). The slurry in the syringe passed through the soiled test lumen. In this way very reproducible results can be obtained with the only variable being the solid fraction in the slurry.

Once the cleaning process was carried out, each of the thus cleaned test lumens and the drying control lumens was dried over 48 hours at 56° C. and their weight recorded.

The mass removed by drying, per unit-mass of initial soil, from the drying control tubes is calculated by the following equation and their average determined:

$$Dry_{Cal}=M_{init\ soil}/(M_{tube\ dry}-M_{tube\ unsoiled})$$

The percentage of soil removed is then calculated by the following equation:

$$M_{soil\ removed}=(M_{init\ soil}-((M_{tube\ dry}-\\ M_{tube\ unsoiled})*Dry_{Calave}))/M_{init\ soil}$$

Figure 4:
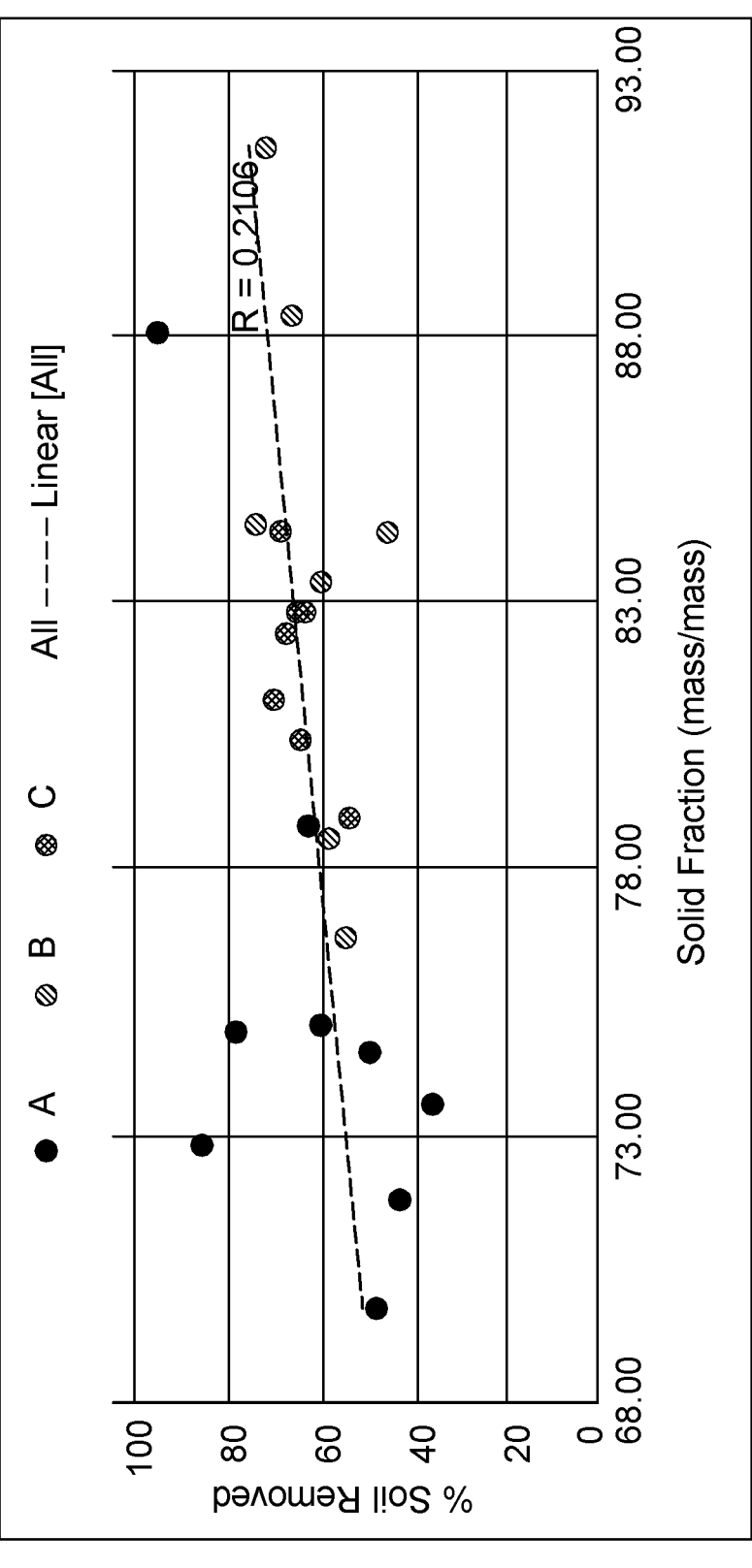
FIG. 4 shows the ability of ice slurries to remove soil from contaminated lumens.

The results are summarised in the attached table and are presented in FIG. 4. The data shows general trend that a higher solid fraction resulted in improved cleaning.

However, it should be noted that as the solid fraction increases, so does the difficulty in pumping the ice slurry. Ice slurries over 85% solids content became difficult to pump and only a small number of experiments with higher solids contents (87%, 88% and 90% solid fraction) could be successfully completed.

Thus, the optimal solids level for slurry cleaning appeared to be at around 80-85% solids content, which produced around 60% soil removal under the controlled conditions used.

| Ice solid Fraction % | Soil Added (g) | Mass Removed (g) | % Mass Removed |
|---|---|---|---|
| 72.78 | 0.6897 | 0.5883 | 85.3 |
| 87.99 | 0.4317 | 0.4116 | 95.4 |
| 75.03 | 0.4407 | 0.2651 | 60.2 |
| 74.51 | 0.3253 | 0.1603 | 49.3 |
| 74.93 | 0.4912 | 0.3824 | 77.9 |
| 78.76 | 0.5354 | 0.3333 | 62.3 |
| 73.55 | 0.3033 | 0.1093 | 36.1 |
| 71.73 | 0.3801 | 0.1642 | 43.2 |
| 69.74 | 0.3897 | 0.1884 | 48.3 |
| 88.34 | 0.3326 | 0.2226 | 66.9 |
| 76.65 | 0.4186 | 0.2285 | 54.6 |

-continued

| Ice solid Fraction % | Soil Added (g) | Mass Removed (g) | % Mass Removed |
|---|---|---|---|
| 78.51 | 0.4105 | 0.2376 | 57.9 |
| 84.30 | 0.4229 | 0.1920 | 45.4 |
| 91.49 | 0.4495 | 0.3210 | 71.4 |
| 83.30 | 0.4670 | 0.2798 | 59.9 |
| 84.41 | 0.4122 | 0.3061 | 74.3 |
| 78.95 | 0.4056 | 0.2211 | 54.5 |
| 80.41 | 0.3737 | 0.2398 | 64.2 |
| 84.31 | 0.3686 | 0.2525 | 68.5 |
| 81.12 | 0.4053 | 0.2848 | 70.3 |
| 82.42 | 0.3728 | 0.2510 | 67.3 |
| 82.81 | 0.4078 | 0.2658 | 65.2 |
| 82.81 | 0.3529 | 0.2241 | 63.5 |

3.4 Visual Inspection of Soil Removal.

Endoscope lumens are of extremely long length in relation to their diameter, which is a factor contributing to the difficulty in their cleaning. In order to better model the cleaning processes in such elongate systems, the cleaning processes were carried out in an endoscope that was specially constructed to have a semi-transparent Teflon tube as a lumen configured to connect with all the internal passageways and having all the necessary external connections and ports present in a commercial endoscope, but without the external casing. This enabled the cleaning of the lumen to be visually examined. The lumen of the uncased endoscope was approximately 1700 mm in length and 4.0 mm inside diameter.

The visible inner workings of the endoscope were particularly useful in examining the efficacy of the suspension methods of the present invention. A clear visual contrast between clean tubing and soiled tubing, which coloured the lumen dark red or brown where present in the lumen enabled a rapid assessment of the usefulness of each slurry. The slurry displaces the red soil from the interior lumen, changing the exterior appearance of the Teflon tube as it does so. This enables the progress of the cleaning along the tube to be monitored readily. When the soil is fully removed, the tube is colourless in appearance and can be compared against a control unsoiled lumen.

After the required volume of slurry had been applied, water could be passed through the lumen to remove ice and facilitate subsequent drying.

The invention claimed is:

1. A method of cleaning a contaminated surface of an interior of an elongate lumen of an endoscope, the method comprising the steps of:
   cooling a liquid mixed with a freezing point depressant within a storage container to form ice particles;
   operating an auger to stir the liquid and the freezing point depressant in the storage container and to scrape the ice particles from sides of the storage container to provide the ice particles with a particle size of 1 to 250 microns to form an ice slurry comprising the ice particles, the liquid, the freezing point depressant, and an ice fraction of 80-85% by volume; and
   flowing the ice slurry into the elongate lumen and along the contaminated surface to remove contaminant from the contaminated surface.

2. A method according to claim 1 comprising:
   flowing the ice slurry into the elongate lumen continuously in a single direction.

3. A method according to claim 2 comprising:
   flowing the ice slurry through the elongate lumen continuously in the single direction at a flow speed that is less than 10 centimeters per second.

4. A method according to claim 1 comprising:
   pulsing the ice slurry through the elongate lumen to alternate between flowing the ice slurry through the elongate lumen and resting the ice slurry within the elongate lumen.

5. A method according to claim 1 further including:
   rinsing the elongate lumen.

6. A method according to claim 1 wherein the liquid comprises water.

7. A method according to claim 1 wherein the freezing point depressant is one of ethanol, propylene glycol or salt brine.

8. A method according to claim 1 wherein said operating the auger to stir the liquid and the freezing point depressant in the storage container and to scrape the ice particles from the sides of the storage container comprises:
   operating the auger to provide the ice particles with a particle size of approximately 10 to 50 microns in the ice slurry.

9. A method according to claim 1 wherein the ice slurry consists essentially of the ice particles, water, and the freezing point depressant.

10. A method, comprising:
   adding a liquid and a freezing point depressant into a storage container;
   cooling the liquid and the freezing point depressant to form ice particles;
   operating an auger to stir the liquid and the freezing point depressant in the storage container and to scrape the ice particles from sides of the storage container to provide the ice particles with a rounded profile and a particle size of 1 to 250 microns to form an ice slurry comprising the ice particles, the liquid, the freezing point depressant, and an ice fraction of 80-85% by volume; and
   flowing the ice slurry into an elongate lumen to remove contaminant from an interior surface of the elongate lumen.

11. A method according to claim 10 wherein said adding the liquid and the freezing point depressant into the storage container comprises:
   adding the liquid into the storage container; and
   adding the freezing point depressant into the liquid in the storage container.

12. A method according to claim 10 wherein said operating the auger to stir the liquid and the freezing point depressant in the storage container and to scrape the ice particles from the sides of the storage container comprises:
   operating the auger to provide the ice particles with a particle size of approximately 10 to 50 microns in the ice slurry.

13. A method according to claim 10 wherein said flowing the ice slurry into the elongate lumen to remove contaminant from the interior surface of the elongate lumen comprises:
   pulsing the flow of the ice slurry through the elongate lumen.

14. A method, comprising the steps of:
   cooling a liquid mixed with a freezing point depressant within a storage container to form ice particles;
   stirring the liquid and scraping the ice particles from sides of the storage container via an auger to provide the ice particles with a particle size of 1 to 250 microns and with a rounded profile to form an ice slurry comprising the ice particles, the liquid, the freezing point depressant, and an ice fraction of 80-85% by volume; and flowing the ice slurry into an elongate lumen to remove contaminant from an interior surface of the elongate lumen.

15. A method according to claim 14 wherein said flowing the ice slurry into the elongate lumen comprises:

pulsing the ice slurry through the elongate lumen.

16. A method according to claim 14 wherein said stirring the liquid and scraping the ice particles from the sides of the storage container comprises:

stirring the liquid and scraping the ice particles from the sides of the storage container to provide the ice particles with a particle size of approximately 10 to 50 microns in the ice slurry.

* * * * *